United States Patent [19]

Howard

[11] 4,450,405
[45] May 22, 1984

[54] ALLOY TESTING APPARATUS USING EDDY CURRENT CONDUCTIVITY PROBE

[75] Inventor: Bruce S. Howard, Seattle, Wash.

[73] Assignee: The Boeing Company, Seattle, Wash.

[21] Appl. No.: 168,625

[22] Filed: Jul. 14, 1980

[51] Int. Cl.³ .................... G01N 27/72; G01R 33/12; G05B 19/02

[52] U.S. Cl. .................................. 324/234; 324/226; 324/228; 364/580

[58] Field of Search ............... 324/225, 228, 233, 234, 324/236, 239, 326–329, 226, 222; 331/65; 364/507, 550, 579–581, 480

[56] References Cited

U.S. PATENT DOCUMENTS

| 3,896,371 | 7/1975 | Hametta | 324/327 |
|---|---|---|---|
| 4,074,186 | 2/1978 | Flaherty | 324/225 |
| 4,130,792 | 12/1978 | Sullivan | 324/236 |
| 4,230,987 | 10/1980 | Mardwinkin | 324/236 |

OTHER PUBLICATIONS

Wagner "Talking Meter Voices DC Voltage Readings", 12/1979, Electronics, pp. 123–124.

Primary Examiner—Gerard R. Strecker
Assistant Examiner—Walter E. Snow
Attorney, Agent, or Firm—Christensen, O'Connor, Johnson & Kindness

[57] ABSTRACT

An analog signal produced in response to eddy current probing of a test part is digitized by an analog-to-digital processor and then entered into a microprocessor-based computer. The digitized conductivity test signal is then acted on by a series of processors including a zero suppress processor which determines if the probe is in contact with a part to be tested and has settled in that position so that an accurate conductivity measurement can be made; a data acquisition processor which receives the conductivity test signal and converts it by means of an interpolation routine into a conductivity signal referenced to a predetermined standard, such as % IACS; a limit processor which compares the converted conductivity test signal with conductivity limits retrieved from the computer memory and based on different alloys and tempers, and which causes the results of such comparison to be displayed on "good/bad" alarms; a peak detection processor which determines that a peak conductivity has been registered after the probe has been disposed in positive contact with the test part; a parts counting processor which responds to the detection of a peak conductivity and in response thereto increments a parts-tested counter; a speech synthesizer processor which is enabled by the peak detection processor and verbally announces, by speech synthesis, the measured peak conductivity; and a recalibration interrupt processor in which the main loop of the programmed microcomputer is interrupted after a predetermined operating interval to disable the test apparatus until it has been recalibrated using a standard of known conductivity.

14 Claims, 7 Drawing Figures

ALLOY TESTING APPARATUS USING EDDY CURRENT CONDUCTIVITY PROBE

BACKGROUND OF THE INVENTION

The invention pertains to conductivity measuring methods and apparatus of the type in which eddy currents are induced into the test part causing a back electro-motive force that produces a measurable change in the impedance of a probe coil.

The use of eddy current probing methods and apparatus to measure the conductivity of metal parts is well known and widely used. For example, the measurement of conductivity in this manner is particularly useful in connection with the quality control testing of structural parts made of alloys, such as those of aluminum, in which excessive deviations in the conductivity of the test part is indicative of an improper mixture of alloyed metals, and/or incorrect heat treatment. Eddy current conductivity testing for defective structures and structural parts is used for example in nondestructive testing of aircraft frame components, especially component structures made of various aluminum alloys.

In the use of known eddy current conductivity testers, the instrument produces an analog or digital signal representing the level of conductivity of the probed part and the operator must correlate such measured data with various reference tables that list acceptable conductivity values for various alloys and their respective temper specifications. The required time and tediousness of this task reduces the rate of part inspection to extremely low productivity levels and are the cause of high operator fatigue and excessive test errors.

Additionally, there is difficulty in keeping track of the number of parts that have been tested by the operator and hence no reliable way of determining whether all of the parts or test locations have been actually inspected. Other shortcomings of available eddy current testers include the lack of accuracy in the test results due to unavoidable, thermal drift of the test apparatus circuitry and the absence of any satisfactory way of ensuring an acceptable degree of calibration of the test instrument during any given batch of tested parts.

Still another difficulty in the use of available eddy current test instruments is the difficulty of reading the conductivity data under adverse probing conditions. The probe which is usually mounted on the end of a test cable, must during certain required inspections, be moved into relatively confined areas in which it is difficult or impossible for the operator to read the output data each time the probe is placed on an inspection point. For example, operator difficulty is encountered in this respect when probing inside an aircraft wing. In such case it is necessary to have an assistant read the instrument and coordinate the test with the probe operator, thereby decreasing the productivity of the inspection process and increasing the likelihood of test errors.

Accordingly, it is an object of the present invention to provide an eddy current test apparatus that overcomes one or more of the above-mentioned difficulties and disadvantages associated with the construction and operation of prior conductivity testers of this kind.

SUMMARY OF THE INVENTION

An apparatus is provided for measuring the conductivity of a test part wherein the apparatus includes an eddy current conductivity sensing probe and cooperating sensing circuit for producing an analog output signal as a function of the part conductivity when the probe is placed in proximity therewith; an analog-to-digital converter for converting the analog conductivity signal to a digitized conductivity signal; digital processing means including a memory for transforming the raw digital conductivity signal into a converted digital conductivity signal referenced to a predetermined standard having an empirically derived, nonlinear relationship to the raw conductivity signal, and further including an interpolation processor for interpolating between stored conductivity values referenced to the above-mentioned standard when the measured conductivity falls between such values; a limit processor for establishing conductivity limits as a function of predetermined input parameters of the test part and for comparing the converted and interpolated digital conductivity signal with the limit values; and, an alarm indicator for indicating when the measured conductivity falls outside the limit values.

In the preferred embodiment, the digital processing of the conductivity signal is initiated in response to a zero suppress processor including a threshold crossover detection function which monitors the level of the raw, unprocessed conductivity signal and produces an enabling signal whenever such signal crosses a threshold reference level indicating that the probe has been moved from a remote position into proximity with the test part. In conjunction with the threshold crossover function, a peak detection processor determines the peak value of the digitized conductivity signal, and a parts-tested counter is incremented in response to the combined events of threshold crossover detection and peak detection. The parts-tested counter thus automatically tallies the number of parts tested by the apparatus.

Also, the preferred embodiment includes a speech synthesizer processor that cooperates with the threshold crossover detector of the zero suppress processor and with the peak detection processor to automatically and verbally announce, by a digitally controlled speech synthesis, known per se, the value of the conductivity detected by the peak detection processor. Thus, an operator using the speech synthesis mode, is able to manipulate the probe in remote areas, where the visual readout devices on the test instrument panel are either difficult or impossible to see, and to thus carry out a sequence of tests in which the results of the test are verbally announced within hearing range of the operator.

To provide a complete disclosure of the invention, reference is made to the appended drawings and following description of one particular and preferred embodiment.

DETAILED DESCRIPTION

Figure 1:
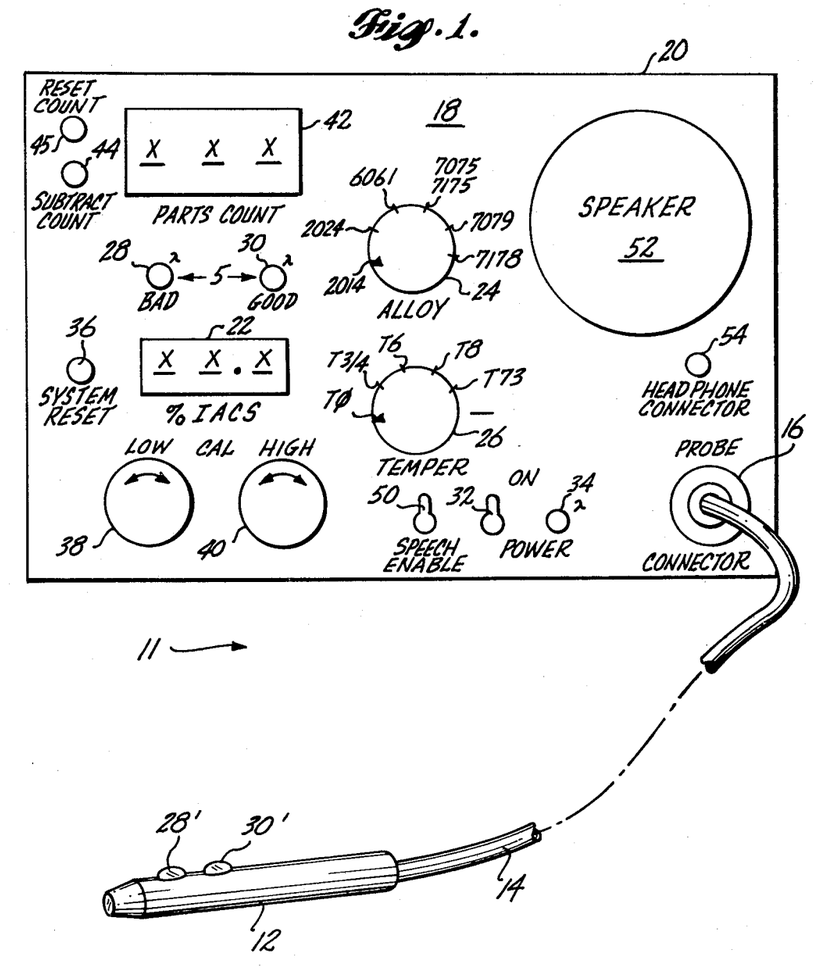
FIG. 1 is a front elevational view of the control panel of the test apparatus and associated probe and probe cable.

With reference to FIG. 1, an eddy current conductivity test apparatus 11 incorporating the principles of the invention is shown to include a manually positionable probe 12 connected by a cable 14 to a connector 16 on the front panel 18 of the instrument's cabinet 20. Mounted on panel 18 are a three digit LED numerical display 22 for displaying the test part conductivity in percent International Annealed Copper Standard (IACS); a multiposition rotary alloy selector switch 24 and an associated multiposition rotary temper selector switch 26; and bad and good LED indicators 28 and 30, respectively, which indicate whether the tested part falls within or outside acceptable conductivity limits. Corresponding bad and good LED indicators 28' and 30' are mounted directly on the body of probe 12 for displaying the results to the operator without requiring visual communication with panel 18.

Additionally, panel 18 includes a power-on switch 32 and an associated power indicator light 34. A pushbutton system reset switch 36 resets the instrument's circuitry following an automatic shutdown caused by a recalibration processor. Also associated with the recalibration processor are low and high calibration adjustment controls 38 and 40, the functions of which are described more fully hereinafter.

A three or more digit LED numerical display 42 registers the number of parts tested during a given test run, and an associated pushbutton count reset switch 45 provides for resetting the count shown on display 42. A pushbutton subtract count switch 44 allows the operator to correct the total count on display 42.

To provide an aural announcement of the measured conductivity, apparatus 11 incorporates a speech synthesizer which when enabled by a panel mounted switch 50, announces the results of each measurement cycle over a panel mounted loudspeaker 52, or through a set of headphones (not shown) which may be connected to headphone connecter 54.

Figure 2:
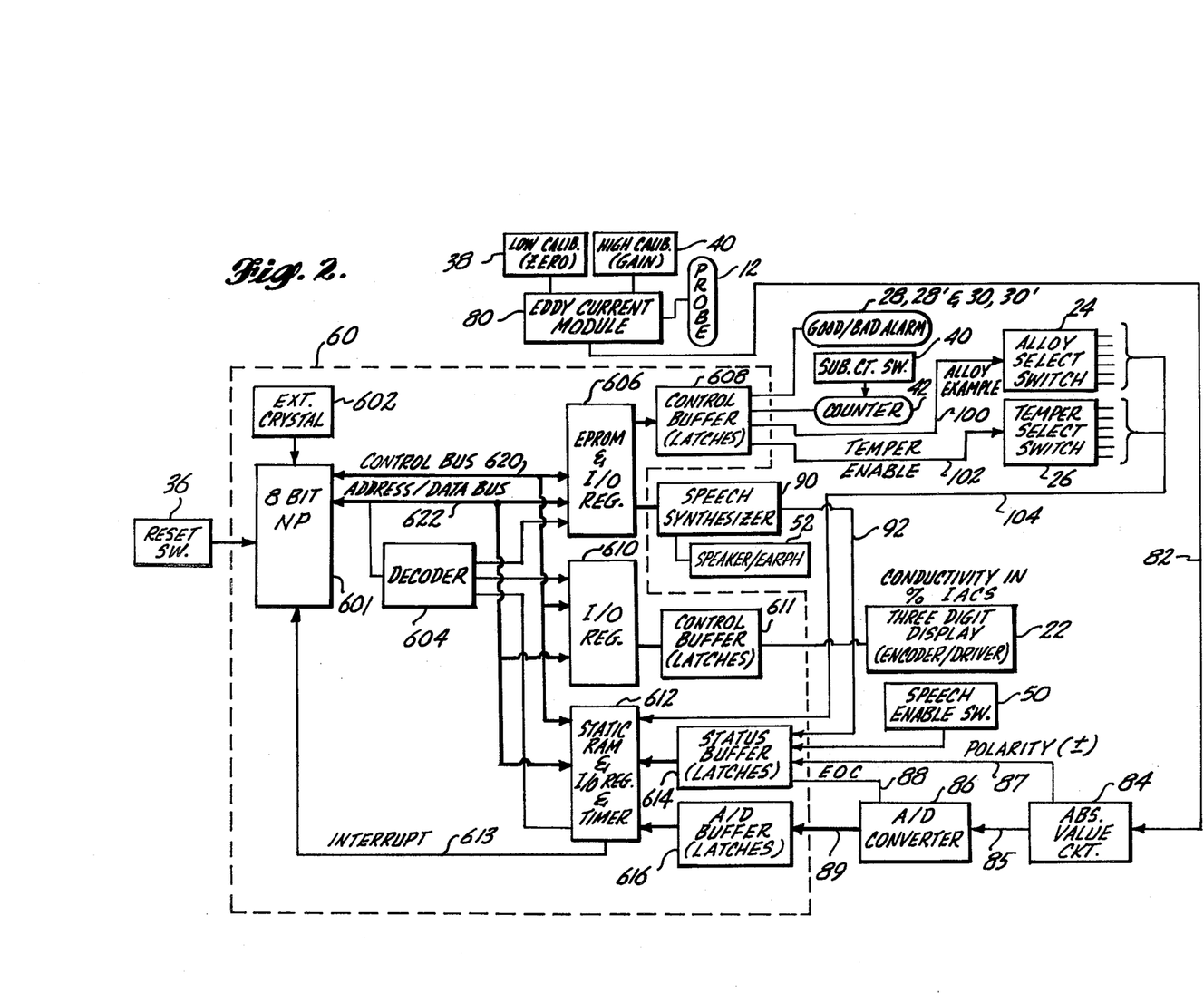
FIG. 2 is a detail block diagram of the microprocessor-based computer and associated input an output devices of the test apparatus.

With reference to FIG. 2, the internal circuitry of test apparatus 11 is shown to include a microprocessor-based computer 60 circumscribed by the dotted line, which is connected to receive raw eddy current measurement data in the form of an analog voltage signal from probe 12 and an associated eddy current module 80 via a signal lead 82. An analog-to-digital conversion is performed on the analog signal output from module 80 by an absolute value circuit 84 and an associated analog-to-digital (A/D) converter 86. The low and high calibration adjustments 38 and 40 are connected to module 80 for direct cooperation therewith to calibrate the analog output signal developed on lead 82 in response to manipulation of probe 12. The remaining components shown on panel 18 and described above in connection with FIG. 1 communicate with microprocessor-based computer 60 through various input/output ports and associated buffer circuits as shown in FIG. 2. Speaker 52 is connected to the output of a speech synthesizer 90 which in turn is operated in response to digital data processed by computer 60 in response to the raw analog measurement signal developed on lead 82 by module 80.

Eddy current module 80 is known per se, and may be commercially purchased from Automation Industries of Los Angeles, Calif., as their eddy current tester Model No. EM2100. Similarly, speech synthesizer 90 is per se a conventional device and a suitable unit for the disclosed embodiment can be obtained from Telesensory Systems, Inc. of Palo Alto, Calif., as their Model S2C, having a 64 word vocabulary in "ASCII."

Microprocessor-based computer 60 incorporates an 8 bit microprocessor 601 and an associated external crystal 602 connected to processor 601; a decoder chip 604, a multifunction integrated circuit chip 606 including an erasable programmable read only memory (EPROM), an input/output (I/O) register which is connected to an output control buffer 608; another integrated circuit chip 610 providing an I/O register which is connected to control buffer 611; and still a third integrated circuit chip 612 that combines the functions of a static random access memory (RAM) and an I/O register and a timer, and which is connected to a tester status buffer 614 and an A/D buffer 616. Microprocessor 601 communicates with chips 606, 610 and 612 over control bus 620 and address/data bus 622 with the assistance of decoder chip 604 which selectively enables these chips to send and receive control and data signals to and from the microprocessor.

In this particular embodiment, microprocessor-based computer uses compatible large scale integrated circuit chips available from Intel Corporation of Santa Clara, Calif. including an 8085 for microprocessor 601, an 8205 for decoder 604, an 8755A for chip 606, an 8255A for register chip 610, an 8155A for the multifunction chip 612 and LS244 buffer for each of buffers 608, 611, 614 and 616. The executive function of microprocessor 601 under the control of a stored program in the EPROM section of chip 606, causes computer 60 to receive the analog-to-digital converted raw eddy current conductivity signal via module 80, lead 82, absolute value circuit 84 and converter 86 through buffers 614 and 616. Absolute value circuit 84 converts a bi-polar analog signal available on lead 82 into a unipolar signal representing the absolute value of the measured conductivity, and that signal is applied to converter 86 over connection 85. Circuit 84 extracts the polarity of the analog signal and produces a polarity indicating bit signal that is fed over connection 87 to status buffer 614 and hence into the register of chip 612. An end of conversion (EOC) signal is produced by A/D converter 86 at the end of a conversion cycle to indicate that the digital data is no longer in a state of transition and accurately reflects the analog input. The EOC signal is in this case communicated over lead 88 to buffer 614 which in turn signals computer 60 that the digital output from converter 86 is ready to be transferred via connection 89 to buffer 616.

The thusly transferred digital data representing a raw eddy current conductivity measurement is processed by computer 60 in the manner described more fully below in connection with FIGS. 3a–3d to develop a processed output value of conductivity that is displayed on display 22 and counter 42. When enabled, speech synthesizer 90 aurally announces the conductivity over speaker 52.

Alloy and temper select switches 24 and 26, respectively, cooperate with alloy and temper enable signals that are produced at the output of control buffer 608 and that act over leads 100 and 102 to interrogate the operator selected positions of switches 24 and 26. The combined position information from the switches is developed on a parallel output bus 104 and is fed therefrom to status buffer 614 where the alloy and temper values are available for causing computer 60 to point to predetermined and previously stored conductivity limits held in the static RAM of chip 612. As described more fully below, the A/D converted conductivity value, after certain preprocessing of this value including an interpolation operation, is compared with the stored conductivity limits associated with the settings of alloy and temper switches 24 and 26, respectively. The good/bad alarms provided by LED indicators 28, 28' and 30, 30' are responsively energized via control buffer 608, in accordance with the results of the comparison signal processing.

The timer component of chip 612 includes an interrupt output that is connected over lead 613 to a trap interrupt of microprocessor 601 to cause an automatic disablement of the test apparatus at the end of a timed interval and to initiate a recalibration sequence, as described more fully hereinafter in connection with FIG. 4. Following recalibration, reset switch 36 on panel 18 of the test apparatus is operated to terminate the interrupt mode and return microprocessor 601 to the main test loop to resume normal processing of the signal from probe 12 and eddy current module 80.

Speech synthesizer 90 is under the control of computer 60 and will only be activated if speech enable switch 50 has been turned on by the operator on control panel 18 (FIG. 1). When enabled, synthesizer 90 operates in response to computer 60 to receive a measured conductivity value from the I/O register of chip 606 and to synthesize the verbal announcement of the particular conductivity in terms of percent IACS. During such speech synthesis by synthesizer 90, a status signal is fed over lead 92 to status buffer 614 to provide needed supervision over the synthesizer operation by computer 60. The input data to synthesizer 90 is in the form of a multibit signal representing the conductivity to be announced. Associated with this multibit data signal is strobing signal information for causing the desired speech synthesis in accordance with the known construction and internal functioning of the commercially available synthesizer 90.

FIGS. 3a, 3b, 3c and 3d together constitute a flowchart of a presently preferred embodiment of the test apparatus 20, by which microprocessor 601 is programmed to provide a plurality of sequentially active signal processors. The functions that these processors perform briefly include: detecting when probe 12 has been placed on the test part; converting a raw analog eddy current conductivity signal to digital form and further transforming the resulting digital signal (by a nonlinear scale version including an interpolation routine) into a transformed digital conductivity signal referenced to a preselected standard, in this case being in % IACS and displaying same; establishing acceptable limits of conductivity, in terms of % IACS, in response to operator set alloy and temper parameters and comparing the transformed digital conductivity signal with such limits and activating good/bad alarms in accordance therewith; detecting a peak value of the transformed digital conductivity signal; automatically advancing a test cycle counter in response to each peak detection for automatically totalizing the number of parts tested; and activating a speech synthesizer (when enabled by switch 50) to aurally announce the test results in terms of % IACS.

Figure 4:
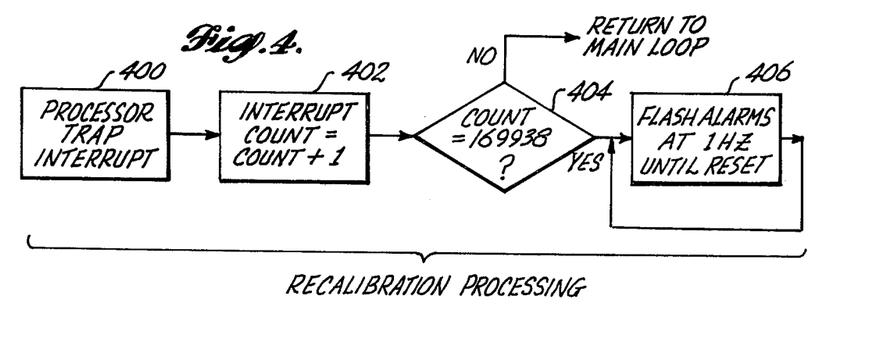
FIG. 4 is a further flowchart showing an interrupt routine that forms another part of the programmed microprocessor-based computer, and which cooperates with the main processing loop shown in FIGS. 3a–3d.

Microprocessor 601 is also programmed in accordance with the flowchart shown in FIG. 4, to incorporate in the preferred embodiment, a recalibration interrupt routine. After a predetermined timed interval of operation of test apparatus 20, microprocessor 601 is programmed so as to respond to an interrupt signal (see connection 613 of FIG. 2) to stop processing the conductivity data and to assume a disabled status. The apparatus remains disabled until reset by switch 36 (FIGS. 1 and 2) following the successful completion of a recalibration procedure as described more fully hereinafter.

Figure 3A:
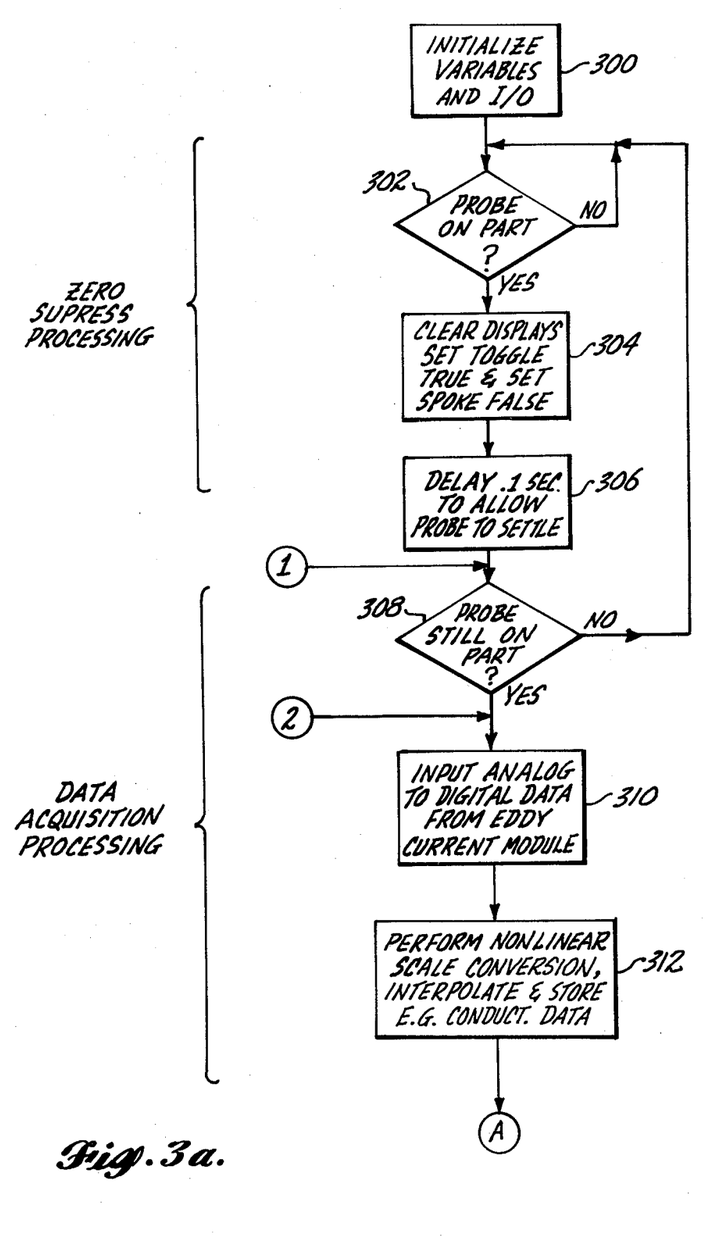
FIGS. 3a, 3b, 3c and 3d collectively form a flowchart of the main program loop of the various processors that are incorporated in the programmed microprocessor-based computer of FIG. 2.

Now with reference to the main processing loop that starts at the top of FIG. 3a, a first instruction block 300 provides for initializing the variables and I/O devices. Included within this instruction are the clearing of I/O register 610 in which a previously measured conductivity value is stored and the resetting of display 22 (FIG. 2), the resetting of the I/O register in chip 606 and the consequent clearing of buffer 608, and the de-energizing of bad/good indicators 28, 28' and 30, 30'. Additionally, the timer in chip 612 for the recalibration interrupt routine is reset to zero to initialize the start of a new interrupt interval. Block 300 is activated in response to each power up of apparatus 11, or by operating reset switch 36.

Following instruction block 300, the program performs a series of decisions and instructions which are collectively referred to as zero suppress processing. This section of the program includes a decision block 302 for determining whether probe 12 (FIG. 2) is on the test part, an instruction block 304 for clearing conductivity display 22 and setting an internal program flag entitled "toggle" to true and setting another internal program flag entitled "spoke" to false, and lastly an instruction block 306 for providing a predetermined delay of less than one second, in this instance being one-tenth of a second, to allow the manually held probe 12 to settle on the test part so as to avoid a premature and hence false reading by the apparatus.

More particularly, decision block 302 includes a comparison instruction in which the digitized conductivity signal from module 80, absolute value circuit 84 and A/D converter 86 (FIG. 2) is compared with a predetermined reference threshold selected to lie somewhere between the level of the conductivity signal that exists when probe 12 is substantially removed from a test part, and an anticipated nominal level of conductivity that exists when probe 12 is in contact with a test part. In this embodiment, the analog signal for module 80 varies between a positive output when probe 12 is remote from a test part, and a negative value of variable magnitude when probe 12 is placed in proximity with a conductive test part. The reference threshold is selected in this embodiment to be at the zero output of module 80. Thus, as probe 12 is moved from a remote position toward a test part, decision block 302 determines when the probe has moved to within sufficient proximity of the part to cause the output signal from module 80 to cross the zero threshold going from a positive to a negative value. Responsively, decision block 302 produces an affirmative answer and the program passes on to instruction block 304. If the decision from block 302 is negative and continues negative upon each pass through block 302, a negative answer is produced causing the program to loop back to the input of block 302 until an affirmative answer is obtained. Until decision block 302 produces an affirmative answer, microprocessor-based computer 60 maintains the input/output register chip 610 at zero, and consequently the conductivity on display 22 of panel 18 is also held at zero, hence the caption for this section of the program "zero suppress processing."

It is noted that the threshold crossing of the analog output from probe 12 and module 80 causes a polarity sign change at the output of absolute value circuit 84, and it is this sign change which serves to detect the probe-on-part proximity.

Following the zero suppress processing of the main program loop shown in FIG. 3a, a data acquisition processing section includes a decision block 308 that determines whether the probe is still on the part; an instruction block 310 by which microprocessor 601 is instructed to input the raw analog-to-digital converted conductivity signal from absolute value circuit 84 and A/D converter 86 into the static ram of chip 612; and an instruction block 312 that performs a nonlinear scale conversion and interpolation on the raw digital data made available by instruction block 310, and stores the result.

If decision block 308 determines that the probe is no longer on the part, as sensed by the converted analog-to-digital signal being positive rather than negative (refer to discussion above for decision block 302), then block 308 will cause the program to loop back up to the input of decision block 302 and repeat the zero supress processing. Otherwise, an affirmative decision from block 308 causes the program loop to continue direction on into instruction block 310.

Block 310 causes the A/D converted raw conductivity signal, and the polarity thereof, from converter 86 and absolute value circuit 84, respectively, to be fed as input data into the ram of chip 612 via status buffer 614 and A/D buffer 616.

Block 312 further processes this data by performing a nonlinear scale conversion on the raw digital conductivity signal. In doing so, an empirically determined array of values in % IACS, correlated to conductivity measured by probe 12 and module 80, are retrieved from memory, and an interpolation is performed between the available stored values in % IACS and the actual digital signal representing the conductivity as measured by probe 12 and module 80. In other words, instruction block 312 first performs a nonlinear scale conversion by determining the bracket values of the raw digital data signal between which the measured conductivity signal lies and retrieving the correlative values of the conductivity in % IACS, which vary in a nonlinear, empirically determined fashion with respect to the measured conductivity. A linear interpolation is then performed on these values to provide a more accurate measure of the conductivity in % IACS.

Computer 60 stores within the static ram of chip 612, an array of digital values for the % IACS, resolved to 1% increments. For each of these % IACS values, chip 612 also stores a correlative, empirically determined digitized value of the raw conductivity corresponding to that measured by probe 12 and module 80. Instruction block 312 determines where the measured conductivity falls in the stored array of raw digital values, and determines the pair of such stored values that bracket the measured conductivity. From the bracket values stored in memory, and the actual, measured conductivity signal received from converter 86, computer 60 retrieves the stored correlative values in terms of IACS and performs a linear interpolation operation to resolve the converted conductivity signal to a final value resolved to less than the 1% IACS increments stored in memory. Although there is a nonlinear empirical relationship between the sets of stored, unconverted conductivity values and the correlative sets of conductivity values converted to the % IACS standard, satisfactory results have been achieved in terms of accuracy of the resulting conductivity measurement by using a linear interpolation process.

Figure 3B:
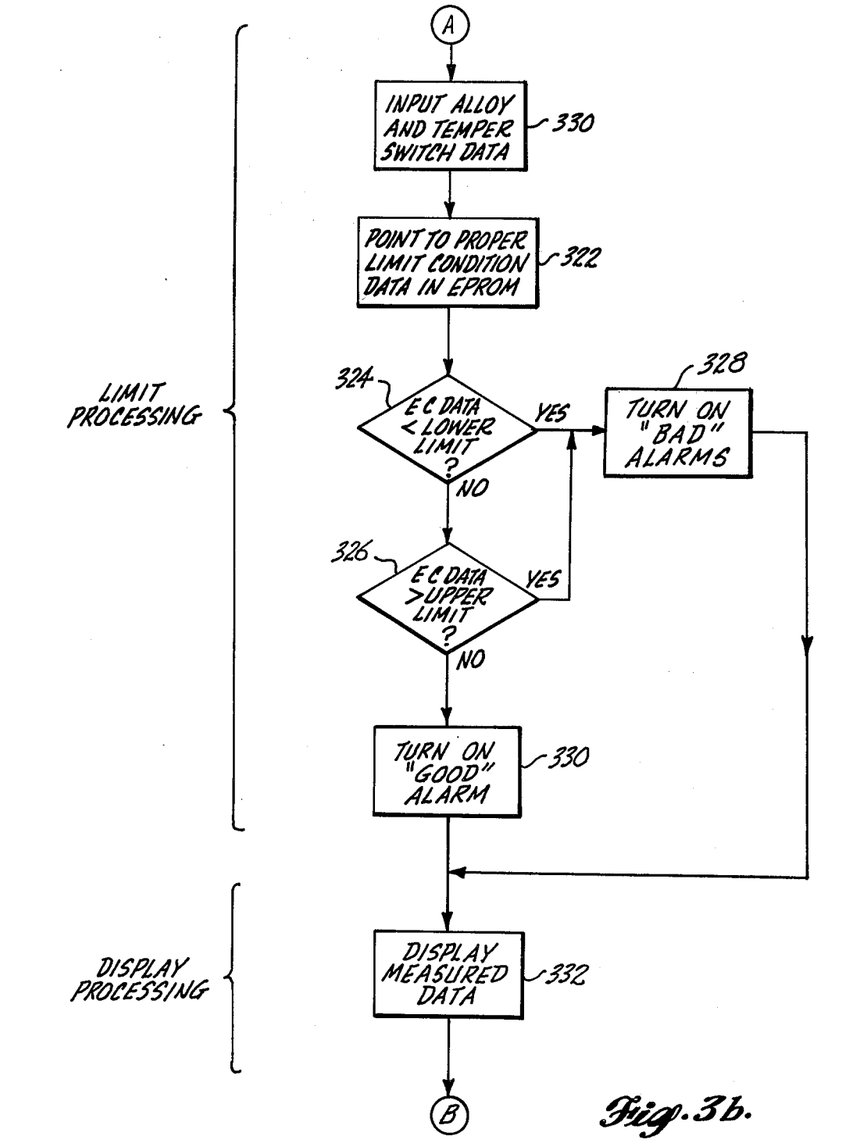

With reference to FIG. 3b, the main program loop now passes into a limit processing section which includes an input alloy and temper switch data instruction block 320, a point to proper limit condition instruction block 322, lower and upper data limit decision blocks 324 and 326, respectively, a turn-on bad alarm instruction block 328 and a turn-on good alarm instruction block 330.

Block 320 interrogates the setting of the alloy select switch 24 (FIG. 2) and in accordance therewith goes to a predetermined memory location in which the full complement of temper settings, selected by switch 26 are available. One of these temper select values is selected by interrogating temper select switch 26 (FIG. 2). The operation of block 320 thus results in a set of addresses that are used by the succeeding instruction block 322 to point to lower and upper limit values stored in the EPROM section of chip 606 (FIG. 2).

If the measured eddy current conductivity signal is lower than the pointed to lower limit developed by block 322, an affirmative decision by block 324 causes instruction block 328 to turn on the bad alarms on panel 18 and probe 12 (FIG. 1). A no decision from block 324 causes the measured and converted eddy current conductivity signal to then be tested by block 326 to determine whether the upper limit is exceeded. If the decision from block 326 is affirmative, then block 328 again causes the bad alarms to be energized. After actuating the bad alarms per instruction block 328, the program loops down to a data display section, discussed below. If the decisions from both block 224 and block 226 are negative, then block 330 causes the good alarms on panel 18 and probe 12 (FIG. 1) to be activated, completing the limit processing section.

Still with reference to FIG. 3b, the display processing section includes a display measured data instruction block 332 which causes the measured and scale converted conductivity signal resulting from instruction block 312 of the data acquisition processing section to be visually displayed by the three digit display 22 mounted on panel 18 as shown in FIG. 2.

Figure 3C:
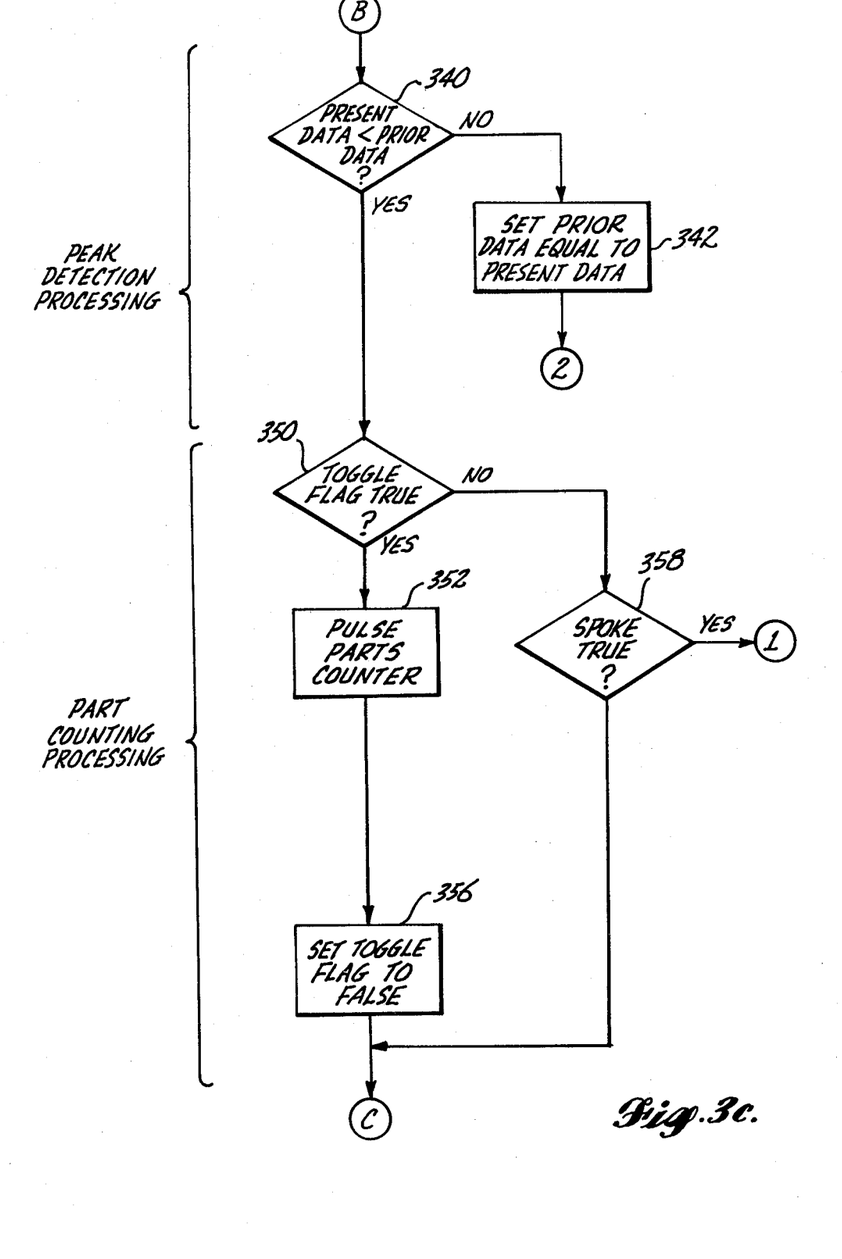

Following the display operation executed by block 332, the main program loop passes on to a peak detection processing section which as shown in FIG. 3c to include a decision block 340 which determines whether the present value of conductivity (determined upon each pass through the program loop) is less than that which existed during the prior pass through the loop, and an instruction block 342 that causes the prior conductivity value to be set equal to the present value. The decision block 340 performs a peak detection operation by comparing the measured and scale converted conductivity value, for each new pass or cycle of the data processing loop with the prior value of the measured and scale converted conductivity value to determine when and at what level the measured conductivity starts decreasing in magnitude.

So long as probe 12 (FIGS. 1 and 2) is remote from the test part and is being moved toward the surface of the part, the repetitive cycling of the data through the program loop will cause each new measured conductivity value to be larger compared to the conductivity value measured during the prior data cycle. Thus, as the probe is moved toward the test part, block 340 continually produces a negative decision and causes instruction block 342 to successively set the prior conductivity value to the new and incrementally larger value. Following instruction block 342, the program loop returns, as indicated by the notation 2 back to the data acquisition processing section where the output of block 342 enters downstream of the probe still on part decision block 308 and upstream of the instruction block 310 that causes the analog-to-digital data to be stored in memory.

So long as probe 12 is in an approach to part phase, the decision from block 340 is negative. However, once the probe has been placed into positive contact with the test part, the value of the measured conductivity will become relatively flat, as a function of time, with a small amount of fluctuation due to natural, and unavoidable shifting of handheld probe. This slight movement of probe 12 is sufficient to cause the measured conductivity data to fluctuate enough so that in response to a very slight decrease, decision block 340 will determine that the present conductivity signal is less than a prior stored value, and will hence produce an affirmative decision. The magnitude of these unavoidable fluctuations in the measured conductivity are inconsequential in terms of the accuracy of the measurement, however, they do provide an effective way of determining the maximum or peak conductivity, after the probe has engaged the part. To guard against false starts, such as where the operator hesitates during the probe approach phase, which could hence cause block 340 to make an affirmative detection of a lower conductivity value, the one-tenth of a second delay provided by instruction block 306 in the zero suppress processing section (FIG. 3*a*) allows the probe to settle on the part before the conductivity data reaches decision block 340 for processing thereby.

With further reference to FIG. 3*c*, when a peak conductivity value has been detected by the peak detection processing section, the program loop passes on to a part counting processing section which includes a toggle flag true decision block 350, a pulse parts counter instruction block 352, a set toggle flag to false instruction block 356 and a spoke true decision block 358. The toggle flag has been previously set true in the zero suppress processing section (FIG. 3*a*) which is situated in an early, upstream section of the program, before the test cycle has been counted and before the processing of the measured conductivity data has been fully executed. Thus, when decision block 350 first receives an affirmative output from decision block 340 of the peak detection processing section, the toggle flag will be true. The decision of block 350 will be affirmative, causing instruction block 352 to pulse the parts counter and hence increment the three digit parts count display 42 provided on panel 18 of the test apparatus 20 (FIG. 1). After executing the instruction of block 352, block 356 sets the toggle flag to false.

Now, when the conductivity data is recirculated in the main program loop, which occurs so long as the probe is detected to be still in contact with the part by decision block 308 (FIG. 3*a*), the false toggle flag will divert the data flow at decision block 350 to the negative branch, thereby precluding the parts counter from being pulsed a second time by block 352 while the probe remains in contact with the same part.

The negative decision from block 350 in this case, loops through a spoke true decision block 358, which determines whether the speech synthesizer processing, herein called the say it processing section, has been completed. A negative decision from block 358 loops the program back to the downstream side of instruction block 356, and hence to the start of the say it processing shown in FIG. 3*d*. An affirmative decision from block 358 returns the program flow to the upstream side of probe still on part decision block 308 of the data acquisition processing section shown in FIG. 3*a*, as signified by the notation 1.

Figure 3D:
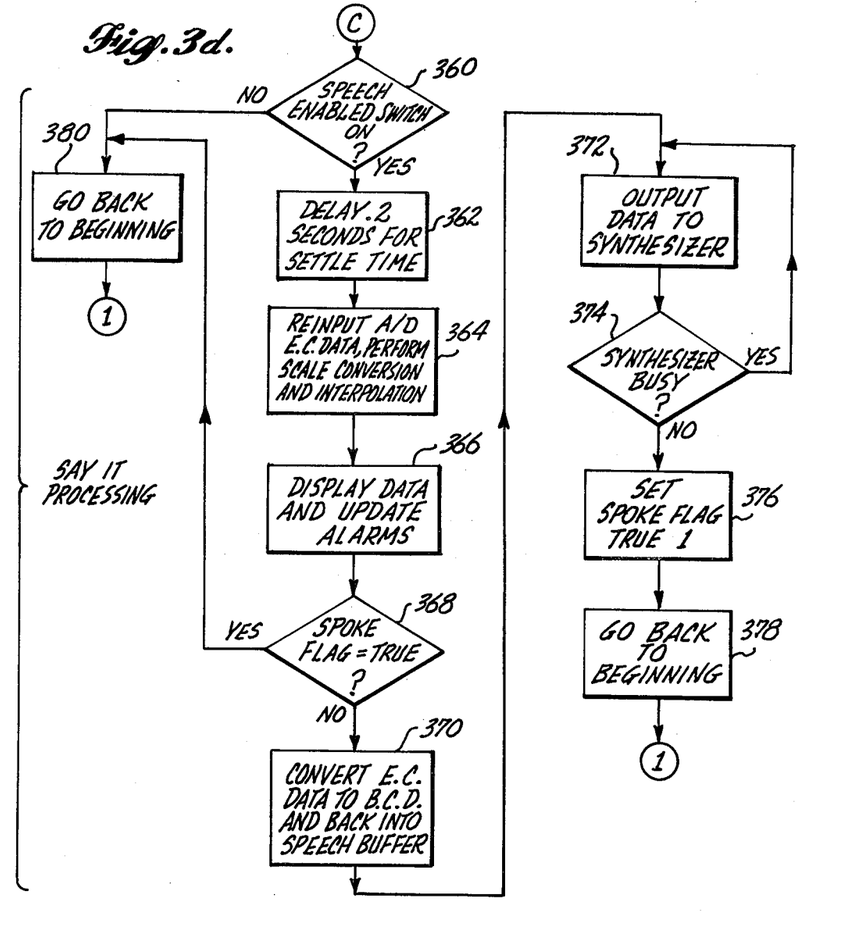

With reference to FIG. 3*d*, the say it processing section includes: a decision block 360 which tests for an on condition of the speech enable switch on panel 18; a sequence of three instruction blocks 362, 364 and 366 responsive to an affirmative decision from block 360, a spoke flag equal true decision block 368 and a set of two successive instruction blocks 370 and 372 responsive to a negative output from decision block 368, a synthesizer busy decision block 374, and a set of successive instruction blocks 376 and 378 that complete this branch of the say it processing routine. Another instruction block 380 returns the program to the beginning (notation 1) in response to a negative decision from the speech enable decision block 360.

During each pass through the say it processing section, block 360 initially determines whether the operator has selected the speech synthesis capability. If switch 50 in panel 18 of apparatus 20 (FIG. 1) is off, then the program flow is diverted from block 360 to instruction block 380 commanding the program to go back to the beginning of the loop at the location marked by the notation numerical 1, which is immediately upstream of the second probe on part decision block 308 of the data acquisition processing section (see FIG. 3*a*). If returned to loop location 1, the program either continues to circulate in the data acquisition processing section, limit processing section, etc., until those routines have been fully executed, or if the probe has been removed from the part, then the program is returned by a negative output from block 308 to the initial probe on part decision block 302 as depicted in FIG. 3*a* and as described above.

If the operator has selected the speech enable, then block 360 as shown in FIG. 3*d* will issue an affirmative response and will cause the instructions of blocks 362, 364 and 366 to be executed in succession. Block 362 introduces a delay, such as two-tenths of a second, in order to allow time for the probe 12 to settle on the test part. The delay in this instance is longer than the initial one-tenth of a second delay provided by block 306 in the zero suppress processing section, in order to ensure that the operator has moved the probe to the desired location and is holding it steady, before the speech synthesis circuitry is activated. Following the delay of block 362, instruction block 364 causes the raw analog signal from probe 12 and module 80 (FIG. 2) to be reintroduced through absolute value circuit 84 and A/D converter 86 into the computer buffers, then to be stored in the static ram of chip 612. This data is then subjected to the same scale conversion and interpolation processes that have been described above in connection with instruction block 312 of the data acquisition processing section shown in FIG. 3*a*.

Thus, during the say it routine, the detected peak value is not in and of itself used as the data output to the synthesizer, rather the analog conductivity signal is reread and reprocessed through the nonlinear scale conversion and interpolation subprocesses, in order to develop a new, updated conductivity value for feeding to the speech synthesizer. During the same pass through the program loop, instruction block 366 causes the reread conductivity data to be displayed on three digit display 22 on the instrument panel 18 (FIG. 1) and causes the "good/bad" alarms 28, 28' and 30, 30' (FIGS. 1 and 2) to be updated if necessary. By rereading the measured conductivity value in this manner, experience has found that the instrument achieves better agreement between the instantaneous display of the conductivity, and the aurally announced conductivity generated by the slower acting speech synthesizer.

Following instruction block 366, decision block 368 determines whether the speech synthesizer has already announced the conductivity results by testing for the spoke flag being true. If the speech synthesizer has already been actuated during an earlier pass through the loop, then a yes answer is produced by block 368 and the program path goes to instruction block 380 to return the program to the beginning as described above. If, however, the program is making an initial pass through the say it processing routine, then a negative answer is produced by decision block 368.

In response to a negative decision by block 368, instruction block 370 converts the eddy current conductivity data from binary to binary coded decimal (BCD) and packs the thusly converted data into a speech buffer (not separately shown) of speech synthesizer 90 (see FIG. 2). Then, block 372 outputs the data in the speech buffer to the operative sections of the speech synthesizer at a predetermined strobe rate, causing the synthesizer to transform the binary coded conductivity data into a synthesized verbal pattern, including three digits and a decimal point, announcing for example, a conductivity of "zero-nine-point-three." Decision block 374 determines whether synthesizer block 372 is busy and if affirmative, the program continues to circulate about block 372 until the speech synthesis is completed and block 374 produces a negative decision. In response to such a negative decision, instruction block 376 sets the spoke flag to true and block 378 directs the program back to the beginning location denoted by numeral 1.

With reference to FIG. 4, the recalibration interrupt processing of computer 60 is shown to include a series of instruction and decision blocks that cofunction with the main program loop to interrupt the latter at a predetermined clock rate, such as once every 5.3 milliseconds as in the presently disclosed embodiment. Thus, the recalibration processing routine includes an instruction block 400 for causing the microprocessor 601 to service the recalibration processing once every clock interval, saving the status and data of the main program so that after the recalibration routine has been executed, the main processing loop can be immediately restored unless instrument recalibration is needed. An instruction block 402 accumulates clock pulses developed by the timer of chip 612 (FIG. 2) for timing the desired recalibration period, and a decision block 404 compares the accumulated count developed by block 402 with a predetermined digital count (in this case 169938) equal to the count equivalent, at the rate of one count every 5.3 milliseconds, of the length of the recalibration period. A block 406 is responsive to an affirmative decision from block 404 for causing the alarm indicators 28, 28' and 30, 30' of the test apparatus (FIGS. 1 and 2) to flash at a recalibration signifying rate of 1 Hz. Alarm indicators 28, 28' and 30, 30' will continue to flash in this manner until the recalibration processor is reset by the system reset switch 36 mounted on the apparatus panel 18 (FIG. 1).

For example, in this embodiment, a recalibration period of 15 minutes has been adopted. After 15 minutes of operation, instruction block 402 will have caused the accumulation of a count of 169938 at the clock pulse rate associated with the timer of chip 612 (FIG. 2). So long as the count accumulated by block 402 falls short of the predetermined total count, decision block 404 will produce a negative decision each time the interrupt routine is serviced, restoring the previous status and returning the control of the microprocessor over to the main program loop described above in connection with FIGS. 3a–3d.

OPERATION

The measurement of material conductivity by eddy current inspection is known to be useful in quality control testing of certain metal alloys such as aluminum. The strength and other physical characteristics of aluminum alloys can vary significantly depending upon the portions of the base metals that compose the alloy. In order to ensure that production parts have the proper alloy composition, it has previously been discovered that an alloy can be tested for the proper mixture by measuring both the material's conductivity and hardness, and comparing these measured parameters with predetermined conductivity and hardness values of a reference alloy having a known alloy mixture and temper. Thus, the eddy current conductivity measurement performed by test apparatus 20 constitutes one step of a twofold test, the other being the measurement of the material hardness. Since the desired or acceptable range of conductivity for any given alloy is a function of the particular alloy mixture and its heat treatment, apparatus 20 includes alloy and temper selector switches 24 and 26 which are set by the operator at the beginning of the test.

The operation of test apparatus 20 will be described by way of example, with reference to a typical quality control task. Assume that the operator of the apparatus is responsible for testing the conductivity of each of a batch of 35 individual test parts (or the equivalent, a series of 35 inspection locations such as on the frame of an aircraft). Initially the operator determines the alloy and temper of the parts to be inspected, and sets switches 24 and 26 on the apparatus panel 18, accordingly. The parts counter 42 is cleared by reset switch 45, and if this is the first use of the apparatus after a recalibration procedure (described below), then system reset switch is also operated. At the option of the operator, the speech enable switch 50 is turned on or off, and in the present example, it will be assumed that switch 50 is turned off and the operator will be visually observing the conductivity display 22 and the "bad/good" indicators 28, 28' and 30, 30'.

Probe 12 is now moved into contact with the test part (or inspection location). As described above, the probe on part decision blocks 302 and 308 (FIG. 3a) detect a zero crossing of the measured conductivity signal developed by probe 12 and module 80 (FIG. 2) which forms an enabling condition for the subsequent processing of the measured digital data. Responsively, the data acquisition processing, limit processing and display processing sections described above in connection with FIGS. 3a–3d, cause the measured conductivity, referenced to % IACS, to be visually presented on display 22. If the computer stored limit conditions are exceeded, the "bad" alarm indicators 28 and 28' will be energized. Otherwise the "good" alarm indicators 30 and 30' will be energized. During this phase of operation, it is noted that the signal processing of the probe sensed conductivity will respond to minute changes in the probe to part proximity, for example as the probe is dragged across the part surface, by updating the % IACS display and limit alarms upon each pass of the signal data through the main processing loop.

During each such pass of the signal data through the processing loop, the peak detection processing section looks for a peak value of the measured conductivity. The peak detection processing serves multiple purposes. For one, it provides a reliable triggering level, in connection with the probe approach and withdrawal cycle (during which the measured conductivity first increases and thereafter decreases) for incrementing the parts counter once to count one tested part or test location. Secondly, the peak detection processing provides for triggering the say it processing section (speech synthesizer) when the synthesizer has been enabled beforehand by switch 50 on panel 18. As described below, the speech synthesizer is relatively slow acting, and hence requires the input data thereto to be frozen temporarily during the speech synthesizing and aural announcement. The triggering of these functions by the peak detection section provides an effective way of coordinating the slow operating speech synthesizer to a rapidly fluctuating conductivity measurement.

Now returning to the above example, each time one of the parts is tested (or locations inspected) the peak detection processing section causes the parts counter to advance one count and present the total on parts counter display 42 on panel 18. When the batch of 35 test parts (or inspection locations) has been completed, the count on display 42 should agree with the number of parts given to the operator for testing. Corrections can be made for false counts by using subtract count switch 44 on panel 18.

If during the inspection of the batch of 35 parts, recalibration is required in response to the recalibration interrupt processing section shown in FIG. 4 and described more fully below, the inspection task is temporarily interrupted, the apparatus is recalibrated, and the testing is resumed by resetting switch 36. The reset of the apparatus does not automatically cause clearing of parts count display count 42. Rather display 42 is cleared independently by count reset switch 45. Thus, the accumulation of the parts count on display 42 may span one or more recalibration periods.

Now it will be assumed that the operator needs the speech synthesizer (say it processing section) of the main program loop as shown in FIG. 3d. This alternative output for the data may for example be required when the operator is testing for conductivity in a confined location, such as inside a hollow wing of an aircraft frame, where it is difficult or impossible to maintain visual contact with display 22. In such a case, the speech enable switch 52 is turned on. When so enabled, the say it processing routine will be triggered in response to the detection of a peak value of the peak detection processing section, which has been described above. The say it processing loop introduces a short delay, for example two-tenths of a second as described above in connection with FIG. 3d, to allow the probe to settle on the part, and then the raw eddy current conductivity data is reintroduced into the microprocessor-based computer 60 and converted to % IACS including interpolation. The revised conductivity value is then used to update the display 22 and for being fed into the input register of the speech synthesizer.

The conductivity data, in the form of a binary coded decimal, is converted by synthesizer 90 to audio speech sounds representing the digits "zero" through "nine" and the word "point." In response to the input data, the synthesizer announces two digits then "point" then a third digit so that the announced results are compatible with visual display 22. During the synthesizer operation, the main program loop is temporarily held up by the synthesizer busy decision block 374 as shown in FIG. 3d. After the conductivity has been announced through speaker 52 (or in the alternative through headphones plugged in to connector 54), the say it processing section is disabled by setting the spoke flag to true. By doing so this section of the program cannot be reactivated until the probe 12 has been withdrawn from the part and placed in contact with another part or another test location, which will re-enable the zero suppress processing section to set the spoke flag false as shown in FIG. 3a. At the same time the toggle flag is set true so that the parts counter can be advanced on the succeeding detection of a peak conductivity value.

Because of inherent problems associated with the measurement of conductivity using an eddy current system, frequent recalibration of the test apparatus is required. The recalibration interrupt processing described above in connection with FIG. 4 causes the test apparatus to become automatically disabled, at the end of a predetermined recalibration period, which in the present embodiment is 15 minutes. After 15 minutes of operation, the main program loop becomes disabled, and the "good/bad" alarms on the instrument panel and probe are flashed at a 1 Hz rate signaling the operator to perform a recalibration process.

Recalibration is carried out by using three or more conductivity standards, of known conductivity. In conjunction therewith, the high and low calibration controls 38 and 40 respectively on panel 18 of the apparatus are adjusted. Low, intermediate and high conductivity standards are preferably used. The low standard, having a conductivity at the low end of the measurement range, is tested using a probe 12 and the low calibration control 38 is adjusted accordingly until display 22 displays the known, reference conductivity value. The operation is repeated on the high calibration standard, by adjusting the high value control 40 to achieve the proper value of display 22. For balance, the intermediate conductivity sample is tested and controls 38 and 40 are tuned slightly to adjust the intermediate range of the apparatus between the high and low conductivity standards. Upon completion of the recalibration procedure, the apparatus is reset by operating switch 36 on panel 18 which clears the previously accumulated interrupt count in block 402 of the recalibration processing section (FIG. 4). The apparatus is now ready for another 15 minutes of testing before the next recalibration interrupt occurs.

While only a particular embodiment has been disclosed herein, it will be readily apparent to persons skilled in the art that numerous changes and modifications can be made thereto, including the use of equivalent means and devices without departing from the spirit of the invention.

The embodiments of the invention in which an exclusive property or privilege is claimed are defined as follows:

1. An apparatus for testing alloy parts, comprising the combination of:

eddy current conductivity sensing means including probe means and circuit means, said circuit means including an output for producing an analog conductivity signal as a function of the conductivity of a test part when said probe means is disposed proximate to the test part;

analog-to-digital conversion means for receiving and converting said analog conductivity signal into a digitized conductivity signal;

digital processing means including memory means for storing the digitized conductivity signal produced by said eddy current conductivity sensing means and said conversion means when said probe means is positioned proximate to the test part and produces a maximum conductivity value for such part, said digital processing means further including conductivity standards memory means for storing standardized conductivity values that are referenced to a predetermined standard and that are correlated to said digitized conductivity signal;

means for retrieving a correlative value of said standardized conductivity values stored in said standards memory means in response to said digitized conductivity signal stored in said memory means when said probe means is proximate a test part, wherein said means for retrieving said correlative values includes interpolation processor means for interpolating between different stored standardized conductivity values, said interpolation processor means producing a processed conductivity signal lying between adjacent, standardized conductivity values stored in said conductivity standards memory means;

limit processor means for producing a limit digital signal of a predetermined limit of conductivity referenced to said standardized conductivity values;

comparison processing means for comparing said processed conductivity signal produced by said interpolation processor means with said limit digital signal representing said limit of conductivity established by said limit processor means; and test indication means for indicating when said processed conductivity signal has a predetermined relationship to said limit digital signal representing said limit of conductivity.

2. The apparatus of claim 1 further comprising an alloy selector switch means and decoder means associated therewith and temper selector switch means and associated decoder means, said limit processor means having limit storage means for storing limit digital signals and having addressing means for addressing a predetermined set of digital limit signals stored in said limit processor means in response to said alloy and temper selector switch means and associated decoder means.

3. The apparatus of claim 2 wherein said alloy selector switch means and said temper selector switch means cofunction to effect a selection of a combination of selected alloy and temper parameters, and wherein said decoder means associated with said alloy selector switch and said temper selector switch include means for decoding said combination of selected alloy and selected temper parameters for addressing a unique set of high and low digital signal limits stored in said limit processor means against which said processed conductivity signal is to be compared.

4. The apparatus of claim 1 further comprising speech synthesizer means having a data input means, a strobe input means and an audio output means, said data input means of said speech synthesizer means being connected to receive said processed conductivity signal produced by said interpolation processor means, and data strobing means connected to said strobe input means of said speech synthesizer means;

peak detection processor means for monitoring said processed conductivity signal produced by said interpolation processor means for determining the occurrence of a peak value as said processed conductivity signal varies with time in response to movement of said probe means relative to a test part; and speech synthesizer enabling processor means operatively associated with said speech synthesizer means and said peak detection processor means for enabling said speech synthesizer means to convert the processed conductivity signal into an audible announcement of the numerical value of conductivity represented by said processed conductivity digital signal in response to said peak detection processor means determining the occurrence of a peak value of said processed conductivity signal.

5. An apparatus for testing alloy parts by eddy current probing for conductivity, comprising the combination of:

eddy current conductivity measurement means including a probe means for producing an analog signal representing the conductivity of the test part when said probe means is moved into proximity therewith;

analog-to-digital conversion means for receiving said analog signal representing the conductivity of the test part and for converting such analog signal to a digitized conductivity signal;

probe-on-part processor means including threshold means for establishing a predetermined threshold level between a first range of levels of said digitized conductivity signal that exists when said probe means is remote from a test part and a second range of levels of said digitized conductivity signal that exists when said probe means is brought into proximity with a test part, said probe-on-part processor means detecting proximity of said probe means to the test part by sensing a charge in level of said digitized conductivity signal in which such signal crosses said predetermined threshold into said second range of levels;

peak detection processor means, controlled by said probe-on-part processor means, for receiving said digitized conductivity signal and detecting a decreasing level thereof when said probe-on-part processor means has detected proximity of said probe means to the test part; and data output means responsive to said peak detection processor means for outputting a peak value of conductivity represented by said digitized conductivity signal.

6. The apparatus of claim 5 further comprising a delay processor means associated with said probe-on-part processor means and said peak detection processor means for delaying operation of said peak detection processor means by a predetermined interval after said digitized conductivity signal crosses said predetermined threshold level into said second range of levels.

7. The apparatus of claim 5 further comprising a tested parts counter means and a parts counter processor means for advancing a count registered by said counter means, said parts processor means being operatively associated with said probe-on-part processor means and said peak detection processor means for causing said counter processor means to advance a count on said counter means in response to said digitized conductivity signal crossing said predetermined threshold level when followed by a detection of a decrease in level of said digitized conductivity signal by said peak detection processor means.

8. The apparatus of claim 7 wherein said data output means comprises a speech synthesizer means having a data input means and a strobing input means, said data input means being coupled to said analog-to-digital conversion means for receiving said digitized conductivity signal, and means for generating a strobe signal for applying a strobing signal to said strobing input means of said speech synthesizer means.

9. The apparatus of claim 8 further comprising delay processor means for delaying the generation of said strobing signal by a predetermined delay interval following the detection of a peak value of said digitized conductivity signal by said peak detection processor means.

10. The apparatus of claim 5 further comprising suppress processor means for causing said data output means to output a zero value of conductivity until said probe on part processor means determines that the digitized conductivity signal has crossed said threshold level.

11. The apparatus of claim 5, further comprising memory means for storing digitized values of conductivity referenced to a predetermined standard and exhibiting a nonlinear relationship with said digitized conductivity signal produced by said analog-to-digital conversion means, and interpolation processor means for converting said digitized conductivity signal to a converted conductivity signal by retrieving and interpolating between stored values of conductivity referenced to said predetermined standard that bracket a digitized conductivity signal produced by said analog-to-digital conversion means, said interpolation processor means producing a converted digitized conductivity signal referenced to said predetermined standard.

12. An apparatus for testing alloy parts by eddy current probing for conductivity, comprising the combination of:
eddy current conductivity measurement means including a probe means for producing an analog signal representing the conductivity of the test part when said probe means is moved into proximity therewith;
analog-to-digital conversion means for receiving said analog signal representing the conductivity of the test part and for converting such analog signal to a digitized conductivity signal;
probe-on-part processor means including threshold means for establishing a predetermined threshold level between a first range of levels of said digitized conductivity signal that exists when said probe means is remote from a test part and a second range of levels of said digitized conductivity signal that exists when said probe means is brought into proximity with a test part, said probe-on-part processor means detecting proximity of said probe means to the test part by sensing a change in level of said digitized conductivity signal in which such signal crosses said predetermined threshold into said second range of levels;
peak detection processor means, controlled by said probe-on-part processor means, for detecting a decreasing level of said digitized conductivity signal when said probe-on-part processor means has detected proximity of said probe means to the test part;
data output means responsive to said peak detection processor means for outputting a peak value of conductivity represented by said digitized conductivity signal; and
tested parts counter means and a parts counter processor means for advancing a count registered by said counter means, said parts counter processor means being operatively associated with said probe-on-part processor means and said peak detection processor means for causing said counter processor means to advance a count on said counter means in response to said probe-on-part processor means detecting said proximity of said probe means to the test part and said peak detection processor means detecting said decreasing level of said digitized conductivity signal.

13. The apparatus of claim 12 wherein said output data means comprises a speech synthesizer means having a data input means and a strobing input means, said data input means being coupled to said analog-to-digital conversion means for receiving said digitized conductivity signal, and means for generating a strobe signal for applying a strobing signal to said strobing input means of said speech synthesizer means.

14. The apparatus of claim 13 further comprising delay processor means for delaying the generation of said strobing signal by a predetermined delay interval following the detection of a peak value of said digitized conductivity signal by said peak detection processor means.

* * * * *

UNITED STATES PATENT AND TRADEMARK OFFICE
CERTIFICATE OF CORRECTION

PATENT NO. : 4,450,405

DATED : May 22, 1984

INVENTOR(S) : Bruce S. Howard

It is certified that error appears in the above-identified patent and that said Letters Patent is hereby corrected as shown below:

Column 16, line 50:     "charge" should be --change--.

Column 17, line 6:     insert --counter-- after "parts"

Signed and Sealed this

First Day of January 1985

[SEAL]

Attest:

GERALD J. MOSSINGHOFF

*Attesting Officer*     *Commissioner of Patents and Trademarks*